(12) United States Patent
Doken et al.

(10) Patent No.: US 7,700,128 B2
(45) Date of Patent: Apr. 20, 2010

(54) SOLID PREPARATION COMPRISING AN INSULIN SENSITIZER, AN INSULIN SECRETAGOGUE AND A POLYOXYETHYLENE SORBITAN FATTY ACID ESTER

(75) Inventors: Kazuhiro Doken, Osaka (JP); Tetsuya Kawano, Osaka (JP); Hiroyoshi Koyama, Osaka (JP); Naoru Hamaguchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 711 days.

(21) Appl. No.: 10/544,581

(22) PCT Filed: Oct. 21, 2004

(86) PCT No.: PCT/JP2004/015958

§ 371 (c)(1),
(2), (4) Date: Apr. 5, 2006

(87) PCT Pub. No.: WO2005/041962

PCT Pub. Date: May 12, 2005

(65) Prior Publication Data

US 2006/0223870 A1    Oct. 5, 2006

(30) Foreign Application Priority Data

Oct. 31, 2003    (JP) .............................. 2003-371679

(51) Int. Cl.
*A61K 9/20*    (2006.01)
(52) U.S. Cl. ..................................................... 424/465
(58) Field of Classification Search ........................ None
See application file for complete search history.

(56) References Cited

U.S. PATENT DOCUMENTS

| | | | | |
|---|---|---|---|---|
| 4,620,974 A | * | 11/1986 | Hersh et al. ................. | 424/453 |
| 5,726,201 A | * | 3/1998 | Fekete et al. ................. | 514/471 |
| 6,599,529 B1 | * | 7/2003 | Skinhøj et al. .............. | 424/458 |
| 2003/0147952 A1 | * | 8/2003 | Lim et al. .................... | 424/468 |
| 2003/0180352 A1 | | 9/2003 | Patel et al. | |
| 2004/0147564 A1 | | 7/2004 | Rao et al. | |
| 2004/0175421 A1 | * | 9/2004 | Gidwani et al. ............. | 424/465 |

FOREIGN PATENT DOCUMENTS

| | | |
|---|---|---|
| EP | 0749751 A2 | 12/1996 |
| FR | 2758461 | 7/1998 |
| GB | 2399015 | 9/2004 |
| JP | 58065213 * | 4/1983 |
| WO | WO 95/12385 | 5/1995 |
| WO | WO 98/11884 | 3/1998 |
| WO | WO 98/31360 | 7/1998 |
| WO | WO 98/36755 | 8/1998 |
| WO | WO 98/57649 | 12/1998 |
| WO | WO 99/03476 | 1/1999 |
| WO | WO 99/03477 | 1/1999 |
| WO | WO 99/03478 | 1/1999 |
| WO | WO 00/27401 | 5/2000 |
| WO | WO 00/28989 | 5/2000 |
| WO | WO 01/41737 A2 | 6/2001 |
| WO | WO 01/51463 | 7/2001 |
| WO | WO 02/04024 | 1/2002 |
| WO | WO 02/055009 | 7/2002 |
| WO | WO 03/066028 A1 | 8/2003 |
| WO | WO 2004/006921 | 1/2004 |
| WO | WO 2004/030700 A1 | 4/2004 |
| WO | WO 2004/067001 A1 | 8/2004 |

OTHER PUBLICATIONS

Database WPI, Section Ch, Week 199007, Derwent Publications Ltd., London, GB; an 1990-048246.

* cited by examiner

*Primary Examiner*—Robert A Wax
*Assistant Examiner*—Bethany Barham
(74) *Attorney, Agent, or Firm*—Foley & Lardner LLP

(57) ABSTRACT

A solid preparation useful as a diabetes-treating agent or the like and excellent in the dissolution properties of an insulin sensitizer and an insulin secretagogue, which comprises an insulin sensitizer, an insulin secretagogue and a polyoxyethylene sorbitan fatty acid ester is provided.

5 Claims, No Drawings

SOLID PREPARATION COMPRISING AN INSULIN SENSITIZER, AN INSULIN SECRETAGOGUE AND A POLYOXYETHYLENE SORBITAN FATTY ACID ESTER

This application is the National Phase filing of International Patent Application No. PCT/JP2004/015958, filed Oct. 21, 2004.

TECHNICAL FIELD

The present invention relates to a solid preparation comprising an insulin sensitizer, an insulin secretagogue and a polyoxyethylene sorbitan fatty acid ester, useful as a diabetes-treating agent.

BACKGROUND ART

The following preparations containing an insulin sensitizer such as thiazolidinediones and an insulin secretagogue were reported:

1) a pharmaceutical composition comprising an insulin sensitivity enhancer in combination with one or more antidiabetics differing from the enhancer in the action mechanism (see EP 749751 A);

2) a composition comprising synergistic effective amounts of a sulfonylurea antidiabetic agent and glitazone antidiabetic agent (see WO 98/36755);

3) a pharmaceutical composition containing an insulin sensitizer, an insulin secretagogue and a pharmaceutically acceptable carrier (see WO 98/57649); and 4) a pharmaceutical composition containing an insulin sensitizer, a sub-maximal amount of an insulin secretagogue, and a pharmaceutically acceptable carrier (see WO 99/03476).

It is preferable that in a solid preparation comprising an insulin sensitizer and an insulin secretagogue, the active ingredients are biologically equivalent to those which are contained in two separate solid preparations as a single active ingredient.

However, the present inventors found a problem in a solid preparation comprising an insulin sensitizer and an insulin secretagogue for the first time, that is, found that said solid preparation had the undesirable dissolution property of an insulin secretagogue, that is, the dissolution rate of an insulin secretagogue from said solid preparation was slower as compared with that from "a solid preparation containing an insulin secretagogue as a single active ingredient".

DISCLOSURE OF INVENTION

The present inventors studied intensively in order to solve the above problem. As a result, they found that the dissolution property of an insulin secretagogue could be improved by incorporating a polyoxyethylene sorbitan fatty acid ester in the solid preparation and accordingly completed the present invention.

That is, the present invention provides (1) a solid preparation comprising an insulin sensitizer, an insulin secretagogue and a polyoxyethylene sorbitan fatty acid ester;

(2) the solid preparation according to the above (1), wherein the insulin sensitizer is pioglitazone hydrochloride;

(3) the solid preparation according to the above (1), wherein the insulin secretagogue is a sulfonylurea agent;

(4) the solid preparation according to the above (3), wherein the sulfonylurea agent is glimepiride;

(5) the solid preparation according to the above (1), wherein the polyoxyethylene sorbitan fatty acid ester is Polysorbate 80;

(6) a solid preparation comprising pioglitazone hydrochloride, glimepiride and Polysorbate 80; and the like.

DETAILED EXPLANATION OF THE INVENTION

An insulin sensitizer used in the present invention means any drug that restores the impaired function of an insulin receptor to the original state and thereby improves the insulin resistance. Specific examples of the insulin sensitizer include pioglitazone, rosiglitazone, reglixane (JTT-501), GI-262570, netoglitazone (MCC-555), balaglitazone (DRF-2593), MB-13.1258, 5-(2,4-dioxothiazolidin-5-ylmethyl)-2-methoxy-N-[4-(trifluoromethyl)benzyl]benzamide (KRP-297), rivoglitazone (CS-011), FK-614, compounds described in WO99/58510 (e.g. (E)-4-[4-(5-methyl-2-phenyl-4-oxazolylmethoxy)benzyloxyimino]-4-phenylbutyric acid), tesaglitazar (AZ-242), ragaglitazar (NN-622), Muraglitazar (BMS-298585), ONO-5816, LM-4156, MBX-102, LY-519818, MX-6054, LY-510929, T-131, THR-0921 and the like.

The insulin sensitizer may be in the form of a salt. Such a salt may be a pharmacologically acceptable salt, such as salts with inorganic bases, salts with organic bases, salts with inorganic acids, salts with organic acids, and salts with basic or acidic amino acids.

Preferred examples of the salts with inorganic bases include salts with alkali metals such as sodium and potassium; alkaline earth metals such as calcium and magnesium; aluminum, ammonium and the like.

Preferred examples of the salts with organic bases include salts with trimethylamine, triethylamine, pyridine, picoline, ethanolamine, diethanolamine, triethanolamine, dicyclohexylamine, N,N-dibenzylethylenediamine and the like.

Preferred examples of the salts with inorganic acids include salts with hydrochloric acid, hydrobromic acid, nitric acid, sulfuric acid, phosphoric acid and the like.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferred examples of the salts with basic amino acids include salts with arginine, lysine, ornithine and the like.

Preferred examples of the salts with acidic amino acids include salts with aspartic acid, glutamic acid and the like.

The insulin sensitizer may be anhydrous or hydrous.

The insulin sensitizer is preferably pioglitazone or a salt thereof (preferably, hydrochloride) or rosiglitazone or a salt thereof (preferably, maleate) and more preferably pioglitazone hydrochloride.

The insulin sensitizer used in the present invention may be a mixture of two or more insulin sensitizers at an appropriate proportion.

An insulin secretagogue used in the present invention includes sulfonylurea agents (e.g. tolbutamide, glibenclamide, gliclazide, chlorpropamide, tolazamide, acetohexamide, glyclopyramide, glimepiride, glipizide, glybuzole) and non-sulfonylurea insulin secretagogues (e.g. repaglinide, nateglinide, mitiglinide or its calcium salt hydrate).

The insulin secretagogue may be in the salt form similar to that of the above-mentioned insulin sensitizer and may be either anhydrous or hydrous.

The insulin secretagogue is preferably a sulfonylurea agent, more preferably glimepiride.

The insulin secretagogue used in the present invention may be a mixture of two or more insulin secretagogues at an appropriate proportion.

A polyoxyethylene sorbitan fatty acid ester used in the present invention includes Polysorbate 20, Polysorbate 40, Polysorbate 60, Polysorbate 65, Polysorbate 80 and the like.

The polyoxyethylene sorbitan fatty acid ester is preferably Polysorbate 80.

The polyoxyethylene sorbitan fatty acid ester used in the present invention may be a mixture of two or more polyoxyethylene sorbitan fatty acid esters at an appropriate proportion.

If sodium lauryl sulfate, a sucrose stearate ester (HLB16) or polyoxyethylene(160)polyoxypropylene(30)glycol (trade name: Pluronic F68) is used in place of the polyoxyethylene sorbitan fatty acid ester in the solid preparation of the present invention, an excellent improving effect on the dissolution property of an insulin secretagogue can not be achieved.

The solid preparation of the present invention is particularly preferably a solid preparation comprising pioglitazone hydrochloride, glimepiride and Polysorbate 80.

The solid preparation of the present invention may contain additives conventionally used in the pharmaceutical technology field. Such additives include excipients, disintegrants, binders, lubricants, coloring agents, pH adjusters, stabilizers, corrigents, sweetenings, flavors, fluidizing agents and the like. The amounts used of additives are determined in accordance with quantities conventionally used in the pharmaceutical technology field.

Excipients include starches such as corn starch, potato starch, wheat starch, rice starch, partially pregelatinized ($\alpha$) starch, pregelatinized ($\alpha$) starch and porous starch; saccharides or sugar alcohols such as lactose, fructose, glucose, mannitol and sorbitol; anhydrous calcium phosphate, crystalline cellulose, precipitated calcium carbonate, calcium silicate, and the like. Because the solid preparation of the present invention contains a polyoxyethylene sorbitan fatty acid ester, its hardness tends to decrease. Therefore, the solid preparation of the present invention preferably contains crystalline cellulose as an excipient in order to increase the hardness. The amount used of crystalline cellulose is preferably 5 to 60 parts by weight, more preferably 10 to 50 parts by weight based on 100 parts by weight of the solid preparation.

Disintegrants include carboxymethylcellulose, carboxymethylcellulose calcium, carboxymethylstarch sodium, croscarmellose sodium, crospovidone, low-substituted hydroxypropylcellulose, hydroxypropyl starch and the like. The amount used of the disintegrant is preferably 0.5 to 25 parts by weight, more preferably 1 to 15 parts by weight based on 100 parts by weight of the solid preparation.

Binders include hydroxypropylcellulose, hydroxypropylmethylcellulose, povidone (polyvinylpyrrolidone), gum arabic powder and the like. The amount used of the binder is preferably 0.1 to 50 parts by weight, more preferably 0.5 to 40 parts by weight based on 100 parts by weight of the solid preparation.

Lubricants include magnesium stearate, calcium stearate, talc, sucrose fatty acid ester, sodium stearyl fumarate and the like.

Coloring agents include food dyes such as food Yellow No. 5 (sunset yellow, the same as food Yellow No. 6 in the United states), food Red No. 2 and food Blue No. 2; food lake pigments, iron sesquioxide and the like.

PH adjusters include citrate, phosphate, carbonate, tartrate, fumarate, acetate, amino acid salt and the like.

Stabilizers include tocopherol, edetate tetrasodium, nicotinic acid amide, cyclodextrins and the like.

Corrigents include ascorbic acid, citric acid, tartaric acid, malic acid and the like.

Sweetenings include Aspartame, Acesulfame K, thaumatin, saccharin sodium, dipotassium glycyrrhizinate and the like.

Flavors include menthol, peppermint oil, lemon oil, vanillin and the like.

Fluidizing agents include light anhydrous silicic acid, hydrous silicon dioxide and the like. The light anhydrous silicic acid contains hydrous silicon dioxide ($SiO_2 \cdot nH_2O$) (wherein n indicates an integer) as the main constituent and specifically includes Sylysia 320 (trade name; Fuji Silysia Chemical LTD), AEROSIL 200 (trade name, Nippon Aerosil CO., LTD) and the like.

Two or more of the above-mentioned additives may be used as a mixture at an appropriate proportion.

The dosage forms of the solid preparation of the present invention include oral preparations such as tablets (including sublingual tablets and intraorally disintegrating tablets), capsules (including soft capsules and microcapsules), powders, granules and troches; and parenteral preparations such as external preparations (for example, transdermal preparations and ointments), suppositories (for example, rectal suppositories and vaginal suppositories) and pellets. These preparations may be controlled-release preparations such as immediate-release preparations or sustained-release preparations (for example, sustained-release microcapsules). The solid preparation of the present invention is preferably a tablet (preferably a layered tablet).

The solid preparation of the present invention may be in round, caplet or oblong form.

The content of an insulin sensitizer in the solid preparation of the present invention is, for example, 0.01 to 98 parts by weight, preferably 1 to 90 parts by weight per 100 parts by weight of the solid preparation of the present invention.

Specifically, when the insulin sensitizer is pioglitazone hydrochloride, the content of pioglitazone hydrochloride in the solid preparation of the present invention is preferably 0.01 to 70 parts by weight, more preferably 2 to 60 parts by weight per 100 parts by weight of the solid preparation of the present invention.

The content of an insulin secretagogue in the solid preparation of the present invention is, for example, 0.01 to 95 parts by weight, preferably 0.03 to 90 parts by weight per 100 parts by weight of the solid preparation of the present invention.

The content of a polyoxyethylene sorbitan fatty acid ester in the solid preparation of the present invention is, for example, 0.01 to 30 parts by weight, preferably 0.05 to 20 parts by weight, more preferably 0.2 to 1 parts by weight per 100 parts by weight of the solid preparation of the present invention.

When a polyoxyethylene sorbitan fatty acid ester is incorporated into a preparation, the polyoxyethylene sorbitan fatty acid ester is oxidized to generate formaldehyde which may adversely affect the stability of an active ingredient in the preparation. Further, a decrease in the hardness of a preparation is caused by an increase in the content of a polyoxyethylene sorbitan fatty acid ester in the preparation. Therefore, the content of a polyoxyethylene sorbitan fatty acid ester in the preparation of the present invention is preferably the minimum amount which is enough to bring about the desired effect (e.g. improvement in the dissolution property of an insulin secretagogue), for example, 0.7 parts by weight or less per 100 parts by weight of the solid preparation of the present invention.

The solid preparation of the present invention can be produced by formulating an insulin sensitizer, an insulin secretagogue and a polyoxyethylene sorbitan fatty acid ester together with, if necessary, the above-mentioned additives according to a conventional method in the pharmaceutical technology field.

The formulation may be performed by combining mixing, granulation, filling into capsules, compression, coating and the like appropriately. The mixing is performed using a mixer such as a V-shape mixer or a tumbling mixer and the granulation is performed using a granulator such as a high-speed stirring granulator or a fluid bed granulator. The compression is performed, for example, using a single-punch tableting machine or a rotary tableting machine and usually under a pressure of 1 to 35 kN/cm$^2$. The coating is performed, for example, using a film coating machine and a coating base may be, for example, a sugar-coating base, a water soluble film coating base, an enteric film coating base, sustained-release film coating base or the like.

The sugar-coating base may be, for example, saccharide or sugar alcohol such as saccharose or erythritol, and may be also used in combination with one or more species selected from talc, precipitated calcium carbonate, gelatin, gum arabic, pullulan, carnauba wax and the like.

The water soluble film coating base includes cellulose polymers such as hydroxypropylcellulose, hydroxypropylmethylcellulose, hydroxyethylcellulose and methylhydroxyethyl cellulose; synthesized polymers such as polyvinylacetal diethylaminoacetate, aminoalkylmethacrylate copolymer E [Eudragit E (trade name), Roehm Pharma] and povidone (polyvinylpyrrolidone); polysaccharides such as pullulan; and the like.

The enteric film coating base includes cellulose polymers such as hydroxypropylmethylcellulose phthalate, hydroxypropylmethylcellulose acetate succinate, carboxymethylethylcellulose and cellulose acetate phthalate; acrylic acid polymers such as methacrylic acid copolymer L [Eudragit L (trade name), Roehm Pharma], methacrylic acid copolymer LD [Eudragit L-30D55 (trade name), Roehm Pharma] and methacrylic acid copolymer S [Eudragit S (trade name), Roehm Pharma]; natural products such as shellac; and the like.

The sustained-release film coating base includes cellulose polymers such as ethyl cellulose; acrylic acid polymers such as aminoalkylmethacrylate copolymer RS [Eudragit RS (trade name), Roehm Pharma] and ethyl acrylate/methyl methacrylate copolymer suspension [Eudragit NE (trade name), Roehm Pharma]; cellulose acetate; and the like.

Two or more of the above-mentioned coating bases may be mixed at an appropriate proportion and then used. In a coating step, coating additives may be also used.

The coating additives include a light-blocking agent and/or a coloring agent such as titanium dioxide, talc and iron sesquioxide; a plasticizer such as polyethylene glycol, triethyl citrate, castor oil and polysorbates; organic acid such as citric acid, tartaric acid, malic acid and ascorbic acid; and the like.

The coating is performed by a known method, for example, by using a film-coating machine.

The solid preparation of the present invention may be printed with a mark or a letter for discrimination and may have a cleavage line for being divided.

The solid preparation of the present invention is produced preferably by the following processes.

1) After an insulin sensitizer and an insulin secretagogue are mixed together with additives such as excipients, the mixture is granulated while sprayed with a dispersion or solution of a polyoxyethylene sorbitan fatty acid ester (preferably Polysorbate 80) and additives such as binders in a solvent (e.g. water). The resulting granules are mixed with additives such as disintegrants and lubricants and then, if necessary, compressed to produce the solid preparation of the present invention.

2) After an insulin sensitizer is mixed with additives such as excipients, the mixture is granulated while sprayed with a dispersion or solution of an insulin secretagogue, a polyoxyethylene sorbitan fatty acid ester (preferably Polysorbate 80) and additives such as binders in a solvent (e.g. water). The resulting granules are mixed with additives such as disintegrants and lubricants and then, if necessary, compressed to produce the solid preparation of the present invention.

3) After an insulin sensitizer is mixed with additives such as excipients, the mixture is granulated while sprayed with a dispersion or solution of additives such as binders (preferably povidone) in a solvent (e.g. water).

After an insulin secretagogue is mixed with additives such as excipients, the mixture is granulated while sprayed with a dispersion or solution of a polyoxyethylene sorbitan fatty acid ester (preferably Polysorbate 80) and additives such as binders in a solvent (e.g. water).

The granules containing an insulin sensitizer and the granules containing an insulin secretagogue thus obtained are mixed together with additives such as disintegrants and lubricants and then, if necessary, compressed to produce the solid preparation of the present invention.

4) After an insulin sensitizer is mixed with additives such as excipients, the mixture is granulated while sprayed with a dispersion or solution of additives such as binders (preferably povidone) in a solvent (e.g. water).

A dispersion or solution of an insulin secretagogue, a polyoxyethylene sorbitan fatty acid ester (preferably Polysorbate 80) and additives such as binders in a solvent (e.g. water) is granulated by spraying it on additives such as excipients.

The granules containing an insulin sensitizer and the granules containing an insulin secretagogue thus obtained are mixed together with additives such as disintegrants and lubricants and then, if necessary, compressed to produce the solid preparation of the present invention.

5) After an insulin sensitizer is mixed with additives such as excipients, the mixture is granulated while sprayed with a dispersion or solution of additives such as binders (preferably povidone) in a solvent (e.g. water). The resulting granules are mixed with additives such as disintegrants and lubricants to obtain mixed powder.

A dispersion or solution of an insulin secretagogue, a polyoxyethylene sorbitan fatty acid ester (preferably Polysorbate 80) and additives such as binders in a solvent (e.g. water) is granulated by spraying it on additives such as excipients. The resulting granules are mixed with additives such as disintegrants and lubricants to obtain mixed powder.

The mixed powder containing an insulin sensitizer and the mixed powder containing an insulin secretagogue thus obtained are layered and then compressed to produce the solid preparation (a two-layered tablet) of the present invention.

6) After an insulin sensitizer is mixed with additives such as excipients, the mixture is granulated while sprayed with a dispersion or solution of additives such as binders (preferably povidone) in a solvent (e.g. water). The resulting granules are mixed with additives such as disintegrants and lubricants and then compressed into a core-tablet.

A dispersion or solution of an insulin secretagogue, a polyoxyethylene sorbitan fatty acid ester (preferably Polysorbate 80) and additives such as binders in a solvent (e.g. water) is granulated by spraying it on additives such as excipients. The resulting granules are mixed with additives such as disintegrants and lubricants to obtain mixed powder.

The mixed powder thus obtained as an outer layer and the above described core-tablet are compressed to produce the solid preparation (a dry-coated tablet) of the present invention.

7) After an insulin sensitizer is mixed with additives such as excipients, the mixture is granulated while sprayed with a dispersion or solution of additives such as binders (preferably povidone) in a solvent (e.g. water). The resulting granules are mixed with additives such as disintegrants and lubricants and then compressed into a tablet. This tablet is coated with a film solution of an insulin secretagogue, a polyoxyethylene sorbitan fatty acid ester (preferably Polysorbate 80), a coating base and additives such as light-blocking agents to produce the solid preparation (a film-coated tablet) of the present invention.

Among these processes, the above 5) is preferred. A solid preparation obtained by the above 5) is excellent in the dissolution properties of an insulin sensitizer and an insulin secretagogue, and specifically has the excellent dissolution property of an insulin secretagogue which is equivalent to that of "a solid preparation containing an insulin secretagogue as a single active ingredient". A solid preparation obtained by the above 5) is also excellent in the content uniformity of an insulin secretagogue.

Between individual dosage units (e.g. tablets) of the solid preparation of the present invention, there is little variation in the insulin secretagogue content. The solid preparation of the present invention also has good storage stability and exhibits stable medical efficacy.

The solid preparation of the present invention is preferably a solid preparation consisting of "a layer containing an insulin sensitizer" and "a layer containing an insulin secretagogue and a polyoxyethylene sorbitan fatty acid ester".

The "layer containing an insulin sensitizer" preferably further contains excipients (e.g. lactose) and binders (e.g. povidone) and further may contain disintegrants (e.g. croscarmellose sodium) and lubricants (e.g. magnesium stearate). When the "layer containing an insulin sensitizer" contains povidone as a binder, a solid preparation which is excellent in dissolution of an insulin sensitizer from said solid preparation, for example, a solid preparation which has a stable dissolution pattern of an insulin sensitizer and wherein there is little difference in the dissolution pattern (in particular, the dissolution pattern in the beginning of the dissolution) between individual dosage units of said solid preparation, is obtained.

The insulin sensitizer of the "layer containing an insulin sensitizer" is preferably pioglitazone hydrochloride.

The "layer containing an insulin secretagogue and a polyoxyethylene sorbitan fatty acid ester" preferably further contains excipients (e.g. lactose, crystalline cellulose, or a mixture thereof) and binders (e.g. hidroxypropylcellulose) and further may contain disintegrants (e.g. croscarmellose sodium) and lubricants (e.g. magnesium stearate). When the "layer containing an insulin secretagogue and a polyoxyethylene sorbitan fatty acid ester" contains crystalline cellulose as an excipient, a solid preparation with increased hardness, for example, a solid preparation which does not crack or chip when it is formulated, transferred, dispensed or administered, is obtained.

The insulin secretagogue and the polyoxyethylene sorbitan fatty acid ester of the "layer containing an insulin secretagogue and a polyoxyethylene sorbitan fatty acid ester" are preferably glimepiride and Polysorbate 80, respectively.

The above-mentioned "solid preparation consisting of a layer containing an insulin sensitizer and a layer containing an insulin secretagogue and a polyoxyethylene sorbitan fatty acid ester" is preferably a solid preparation (preferably a layered tablet) obtained by the above 5).

The solid preparation of the present invention can be orally or parenterally administered to mammals (for example, mice, rats, rabbits, cats, dogs, bovines, horses, monkeys, human being, and others) safely.

The solid preparation of the present invention is useful as a preventing and treating agent for, for example, diabetes (e.g., type 1 diabetes, type 2 diabetes, gestational diabetes, etc.), hyperlipemia (e.g., hypertriglyceridemia, hypercholesterolemia, hypo-high density lipoproteinemia, postprandial hyperlipemia, etc.), impaired glucose tolerance (IGT), diabetic complications [e.g., neuropathy, nephropathy, retinopathy, cataract, macroangiopathy, osteopenia, diabetic hyperosmolar coma, infections (e.g., respiratory tract infection, urinary tract infection, alimentary canal infection, dermal soft tissue infection, inferior limb infection, etc.), diabetic gangrene, xerostomia, hypacusis, cerebrovascular disorder, peripheral blood circulation disorder, etc.], obesity, osteoporosis, cachexia (e.g., cancerous cachexia, tuberculous cachexia, diabetic cachexia, hemopathic cachexia, endocrinopathic cachexia, infectious cachexia, or AIDS-induced cachexia), fatty liver, hypertension, polycystic ovary syndrome, renal diseases (e.g., diabetic nephropathy, glomerulonephritis, glomerulosclerosis, nephrotic syndrome, hypertensive nephrosclerosis, end-stage renal diseases, etc.), muscular dystrophy, myocardial infarction, angina pectoris, cerebrovascular disorder (e.g., cerebral infarction, cerebral stroke), insulin resistant syndrome, syndrome X, dysmetabolic syndrome, hyperinsulinemia, hyperinsulinemia-induced sensory disorder, tumors (e.g., leukemia, breast cancer, prostate cancer, skin cancer, etc.), irritable bowel syndrome, acute/chronic diarrhea, inflammatory diseases [e.g., Alzheimer's disease, chronic rheumatoid arthritis, spondylitis deformans, arthritis deformans, lumbago, gout, postoperative or traumatic inflammation, swelling, neuralgia, pharyngitis, cystitis, hepatitis (including non-alcoholic fatty hepatitis), pneumonia, pancreatitis, inflammatory colonic disease, ulcerative colitis, etc.], visceral obesity syndrome, or arteriosclerosis (e.g., atherosclerosis, etc.).

The solid preparation of the present invention is also useful for secondary prevention of the above-mentioned various diseases (e.g., secondary prevention of cardiovascular events such as myocardial infarction) and inhibition of progression in these diseases (e.g., inhibition of the progression from impaired glucose tolerance to diabetes, or inhibition of the progression to arteriosclerosis in diabetic patients).

A dose of the solid preparation of the present invention may be an effective amount based on an insulin sensitizer and an insulin secretagogue contained in said solid preparation.

The effective amount of an insulin sensitizer is usually 0.01 to 500 mg/day, preferably 0.1 to 100 mg/day per adult (60 kg body weight).

In the case where the insulin sensitizer is pioglitazone hydrochloride, the effective amount of pioglitazone hydrochloride is usually 7.5 to 60 mg/day, preferably 15 to 60 mg/day per adult (60 kg body weight).

In the case where the insulin sensitizer is rosiglitazone maleate, the effective amount of rosiglitazone maleate is usually 1 to 12 mg/day, preferably 2 to 8 mg/day per adult (60 kg body weight).

The effective amount of an insulin secretagogue is usually 0.01 to 10000 mg/day, preferably 0.1 to 5000 mg/day per adult (60 kg body weight).

In the case where the insulin secretagogue is a sulfonylurea agent (preferably glimepiride), the effective amount of a sulfonylurea agent (preferably glimepiride) is usually 0.1 to 100 mg/day, preferably 1 to 10 mg/day per adult (60 kg body weight).

The solid preparation of the present invention is administered preferably once or twice a day, more preferably once a day to the above-mentioned mammals. Particularly, the solid preparation of the present invention is preferably administered once before breakfast to the mammals.

The solid preparation of the present invention is preferably a solid preparation containing pioglitazone hydrochloride and glimepiride, more preferably a tablet (preferably a layered tablet) containing 30 mg of pioglitazone hydrochloride and 2 mg of glimepiride, a tablet (preferably a layered tablet) containing 30 mg of pioglitazone hydrochloride and 4 mg of glimepiride, a tablet (preferably a layered tablet) containing 45 mg of pioglitazone hydrochloride and 4 mg of glimepiride, or the like.

The solid preparation of the present invention may be used in combination with one or more drugs (hereinafter referred to as concomitant drugs) selected from diabetic treating agents, diabetic complication treating agents, hyperlipemia treating agents, hypotensive drugs, anti-obesity drugs, diuretics and antithrombotic drugs. These active components may be low-molecular compounds or macromolecular protein, polypeptides, antibodies, vaccines or the like. Two or more of these active components may be mixed at an appropriate proportion for use.

The diabetic treating agents include insulin preparations (e.g., animal-derived insulin preparations extracted from bovine or swine pancreas; human insulin preparations which are synthesized with genetic engineering using *Escherichia coli* or yeast; insulin zinc; protamine insulin zinc; insulin fragments or derivatives (for example, INS-1) etc.), α-glucosidase inhibitors (e.g., voglibose, acarbose, miglitol, emiglitate, etc.), biguanide agents [e.g., phenformin, metformin, buformin, or their salts (e.g., hydrochloride, fumarate, succinate), etc.], dipeptidylpeptidase IV inhibitors (e.g., NVP-DPP-278, PT-100, NVP-DPP-728, LAF237, P32/98, P93/01, TS-021 etc.), β3 agonists (e.g., CL-316243, SR-58611-A, UL-TG-307, SB-226552, AJ-9677, BMS-196085, AZ-40140, etc.), amylin agonists (e.g., pramlintide etc.), phosphotyrosine phosphatase inhibitors (e.g., sodium vanadate etc.), glyconeogenesis inhibitors (e.g., glycogen phosphorylase inhibitors, glucose-6-phosphatase inhibitors, glucagon antagonists, etc.), sodium-glucose cotransporter (SGLUT) inhibitors (e.g., T-1095 etc.), 11β-hydroxysteroid-dehydrogenase inhibitors (e.g., BVT-3498), adiponectin or agonists thereof, IKK inhibitors (e.g., AS-2868), leptin sensitivity-improving agents, somatostatin receptor agonists (e.g., compounds described in WO01/25228, WO03/42204, WO98/44921, WO98/45285, and WO99/22735), glucokinase activators (e.g., Ro-28-1675) and the like.

The diabetic complication treating agents include aldose reductase inhibitors (e.g., tolrestat, epalrestat, zenarestat, zopolrestat, minalrestat, fidarestat (SNK-860), CT-112, etc.), neurotrophic factors (e.g., NGF, NT-3, BDNF, etc.), neurotrophic factor production/secretion promotors [e.g., neurotrophin production/secretion promotors described in WO01/14372, for example, 4-(4-chlorophenyl)-2-(2-methyl-1-imidazolyl)-5-(3-(2-methylphenoxy)propyl)oxazole) etc.], PKC inhibitors (e.g., ruboxistaurin mesylate (LY-333531) etc.), AGE inhibitors (e.g., ALT946, pimagedine, piratoxathin, N-phenacylthiazolium bromide (ALT766), EXO-226, ALT-711, pyridorin, pyridoxamine etc.), reactive oxygen scavengers (e.g., thioctic acid etc.), cerebral vasodilators (e.g., tiapride, mexiletine, etc.), somatostatin receptor agonists (e.g., BIM23190), and apoptosis signal regulating kinase-1 (ASK-1) inhibitors.

The hyperlipemia treating agents include HMG-CoA reductase inhibitors (e.g., pravastatin, simvastatin, lovastatin, atorvastatin, fluvastatin, lipantil, cerivastatin, itavastatin (pitavastatin), rosuvastatin (ZD-4522) or their salts (sodium salts, calcium salts, etc.) etc.), fibrate compounds (e.g., benzafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate, etc.), squalene synthase inhibitors (e.g., the compounds described in WO97/10224, for example, 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepine-3-yl]acetyl]piperidine-4-acetic acid, etc.), ACAT inhibitors (e.g., Avasimibe, Eflucimibe, etc.), anion-exchange resins (e.g., cholestyramine etc.), probucol, nicotinic acid drugs (e.g., nicomol, niceritrol, etc.), ethyl icosapentate, phytosterol (e.g., soysterol), γ-oryzanol, etc.), and the like.

The hypotensive drugs include angiotensin converting enzyme inhibitors (e.g., captopril, enalapril, delapril, etc.), angiotensin II antagonists (e.g., candesartan, cilexetil, losartan, eprosartan, valsartan, telmisartan, irbesartan, tasosartan, olmesartan medoxomil, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, etc.), calcium antagonists (e.g., manidipine, nifedipine, nicardipine, amlodipine, efonidipine, etc.), potassium channel openers (e.g., levcromakalim, L-27152, AL 0671, NIP-121, etc.), clonidine and the like.

The anti-obesity drugs include anti-obesity drugs acting on the central nervous system [e.g., dexfenfluramine, fenfluramine, phentermine, sibutramine, amphepramone, dexanphetamine, mazindol, phenylpropanolamine, clobenzorex; MCH receptor antagonists (e.g., SB-568849, SNAP-7941, compounds described in WO01/82925 and WO01/87834) etc.); neuropeptide Y antagonists (e.g., CP-422935); cannabinoid receptor antagonists (e.g., SR-141716, SR-147778); ghrelin antagonists; 11β-hydroxysteroiddehydrogenase inhibitors (e.g., BVT-3498), etc.], pancreatic lipase inhibitors (e.g., orlistat, ATL-962 etc.), β3 agonists (e.g., CL-316243, SR-58611-A, UL-TG-307, SB-226552, AJ-9677, BMS-196085, AZ-40140, etc.), peptidic anorectics (e.g., leptin, CNTF (ciliary neurotrophic factors), etc.), cholecystokinin agonists (e.g., lintitript, FPL-15849, etc.), feeding inhibitors (e.g., P-57) and the like.

The diuretics include xanthine derivatives (e.g., sodium salicylate theobromine, calcium salicylate theobromine, etc.), thiazide agents (e.g., ethiazide, cyclopenthiazide, trichlormethiazide, hydrochlorothiazide, hydroflumethiazide, benzylhydrochlorothiazide, penflutizide, polythiazide, methyclothiazide, etc.), anti-aldosterone drugs (e.g., spironolactone, triamterene, etc.), carbonic anhydrase inhibitors (e.g., acetazolamide, etc.), chlorobenzenesulfonamide drugs (e.g., chlorthalidone, mefruside, indapamide, etc.), azosemide, isosorbide, etacrynic acid, piretanide, bumetanide and furosemide.

The antithrombotic drugs include heparin (e.g., heparin sodium, heparin calcium, dalteparin sodium, etc.), warfarin (e.g., warfarin potassium etc.), anti-thrombin agents (e.g., aragatroban etc.), thrombolytic agents (e.g., urokinase, tisokinase, alteplase, nateplase, monteplase, pamiteplase, etc.), platelet aggregation inhibitors (e.g., ticlopidine hydrochloride, etc.), cilostazol, ethyl icosapentate, beraprost sodium and sarpogrelate hydrochloride and the like.

The timing of administration of the solid preparation of the present invention and a concomitant drug is not limited and they may be administered simultaneously or at staggered times. Alternatively, a single dosage form containing the solid preparation of the present invention and a concomitant drug may be administered to a subject.

A dose of a concomitant drug can be selected appropriately based on the clinical dose. The combination ratio between the solid preparation of the present invention and a concomitant drug can be selected appropriately depending on a subject to be administered, an administration route, disease to be treated, symptoms and a combination of drugs. In the case where a subject to be administered is a human, 0.01 to 100 parts by weight of a concomitant drug may be used per 1 part by weight of the solid preparation.

Thus, by using a concomitant drug, superior effects such as 1) enhanced actions of the solid preparation of the present invention and a concomitant drug (synergistic action of the drugs), 2) reduced doses of the solid preparation of the present invention or a concomitant drug (reduction in doses compared with those when they are administered individually) and 3) reduced adverse effects of the solid preparation of the present invention and a concomitant drug can be obtained.

Hereinafter, the present invention will be explained in detail with reference to Examples and Experimental Examples which are not intended to limit the present invention.

In the following Examples, products that meet the Japanese Pharmacopoeia 14th Edition or Japanese Pharmaceutical Excipients 2003 were used as various additives such as lactose, hydroxypropylcellulose, croscarmellose sodium, magnesium stearate, crystalline cellulose and Polysorbate 80.

EXAMPLE 1

Glimepiride (10 g) was dispersed and suspended in a solution (150 g) of hydroxypropylcellulose (7.5 g) in water and then mixed with Polysorbate 80 (1.5 g). The resulting mixture solution was granulated by spraying it on a mixture of pioglitazone hydrochloride (82.65 g) and lactose (179.35 g) in a fluid bed granulator (LAB-1, manufactured by Powrex Corp.). To a part (28.1 g) of the granules thus obtained, croscarmellose sodium (1.8 g) and magnesium stearate (0.1 g) were added and mixed. The resulting mixture (120 mg) was compressed at a tableting pressure of 1.0 t/cm$^2$ (7.0 mm$\phi$ flat-faced with beveled edge) using Autograph (AG-50 kN, manufactured by Shimadzu Corp.) to obtain a tablet.

EXAMPLE 2

Glimepiride (10 g) was dispersed and suspended in a solution (150 g) of hydroxypropylcellulose (7.5 g) in water and then mixed with Polysorbate 80 (1.5 g). The resulting mixture solution was granulated by spraying it on lactose (272 g) in a fluid bed granulator (LAB-1, manufactured by Powrex Corp.) to obtain granules containing glimepiride.

A mixture of pioglitazone. hydrochloride (82.65 g) and lactose (190.85 g) was granulated while sprayed with a solution (150 g) of hydroxypropylcellulose (7.5 g) in water in a fluid bed granulator (LAB-1, manufactured by Powrex Corp.) to obtain granules containing pioglitazone hydrochloride.

The granules (14.05 g) containing glimepiride and the granules (14.05 g) containing pioglitazone hydrochloride were mixed together with croscarmellose sodium (1.8 g) and magnesium stearate (0.1 g). The mixture thus obtained (240 mg) was compressed at a tableting pressure of 1.0 t/cm$^2$ (8.5 mm$\phi$ flat-faced with beveled edge) using Autograph (AG-50 kN, manufactured by Shimadzu Corp.) to obtain a tablet.

EXAMPLE 3

Glimepiride (12 g) was dispersed and suspended in a solution (180 g) of hydroxypropylcellulose (9 g) in water and then mixed with an aqueous 18% Polysorbate 80 solution (10 g). The resulting mixture solution was granulated by spraying it on lactose (206.4 g) in a fluid bed granulator (LAB-1, manufactured by Powrex Corp.). To a part (22.94 g) of the granules thus obtained, croscarmellose sodium (2.16 g), crystalline cellulose (10.81 g) and magnesium stearate (0.12 g) were added and mixed to obtain mixed powder containing glimepiride.

The mixed powder containing glimepiride thus obtained (120 mg) and mixed powder (120 mg) obtained by mixing the granules (28.1 g) containing pioglitazone hydrochloride obtained in Example 2 with croscarmellose sodium (1.8 g) and magnesium stearate (0.1 g) were compressed in layers at a tableting pressure of 1.0 t/cm$^2$ (8.5 mm$\phi$ flat-faced with beveled edge) using Autograph (AG-50 kN, manufactured by Shimadzu Corp.) to obtain a layered tablet.

EXAMPLE 4

Glimepiride (40 g) was dispersed and suspended in a solution (900 g) of hydroxypropylcellulose (45 g) in water and then mixed with an aqueous 20% Polysorbate 80 solution (45 g). The resulting mixture solution was granulated by spraying it on a mixture of lactose (1052 g) and crystalline cellulose (360 g) in a fluid bed granulator (MP-10, manufactured by Powrex Corp.). This granulation was performed in 7 batches and the resulting granules were mixed. To a part (9370.7 g) of the granules thus obtained, croscarmellose sodium (672 g), crystalline cellulose (1120 g) and magnesium stearate (37.3 g) were added and mixed to obtain mixed powder containing glimepiride.

A mixture of pioglitazone hydrochloride (496 g), lactose (1072 g) and croscarmellose sodium (108 g) was granulated while sprayed with a solution (540 g) of povidone (54 g) in water in a fluid bed granulator (MP-10, manufactured by Powrex Corp.). This granulation was performed in 7 batches and the resulting granules were mixed. To a part (11147.6 g) of the granules thus obtained, croscarmellose sodium (406 g) and magnesium stearate (46.4 g) were added and mixed to obtain mixed powder containing pioglitazone hydrochloride.

The mixed powder (90 mg) containing glimepiride and the mixed powder (120 mg) containing pioglitazone hydrochloride thus obtained were compressed in layers at a tableting pressure of 5.5 kN/punch (8.0 mm$\phi$ convex-faced) using a rotary tableting machine (AQUARIUS 0512LD2AX, manufactured by Kikusui Seisakusho Ltd.) to obtain a layered tablet containing 30 mg of pioglitazone hydrochloride and 2 mg of glimepiride per tablet.

EXAMPLE 5

The mixed powder (180 mg) containing glimepiride and the mixed powder (120 mg) containing pioglitazone hydrochloride obtained in Example 4 were compressed in layers at a tableting pressure of 7.8 kN/punch (9.0 mm$\phi$ convex-faced) using a rotary tableting machine (AQUARIUS 0512LD2AX, manufactured by Kikusui Seisakusho Ltd.) to obtain a layered tablet containing 30 mg of pioglitazone hydrochloride and 4 mg of glimepiride per tablet.

EXAMPLE 6

The mixed powder (180 mg) containing glimepiride and the mixed powder (180 mg) containing pioglitazone hydrochloride obtained in Example 4 were compressed in layers at a tableting pressure of 7.6 kN/punch (9.5 mmφ flat-faced with beveled edge) using a rotary tableting machine (AQUARIUS 0512LD2AX, manufactured by Kikusui Seisakusho Ltd.) to obtain a layered tablet containing 45 mg of pioglitazone hydrochloride and 4 mg of glimepiride per tablet.

COMPARATIVE EXAMPLE

Glimepiride (12 g) was dispersed and suspended in a solution (180 g) of hydroxypropylcellulose (9 g) in water. The resulting mixture solution was granulated by spraying it on lactose (208.2 g) in a fluid bed granulator (LAB-1, manufactured by Powrex Corp.). To a part (22.93 g) of the granules thus obtained, croscarmellose sodium (2.17 g), crystalline cellulose (10.80 g) and magnesium stearate (0.12 g) were added and mixed to obtain mixed powder containing glimepiride.

The mixed powder containing glimepiride thus obtained (120 mg) and mixed powder (120 mg) obtained by mixing the granules containing pioglitazone hydrochloride obtained in Example 2 (28.1 g) with croscarmellose sodium (1.8 g) and magnesium stearate (0.1 g) were compressed in layers at a tableting pressure of 1.0 t/cm² (8.5 mmφ flat-faced with beveled edge) using Autograph (AG-50 kN, manufactured by Shimadzu Corp.) to obtain a layered tablet.

EXPERIMENTAL EXAMPLE 1

Dissolution of glimepiride from the tablets of Example 3 and Comparative Example was tested by a paddle method (50 rpm) using 900 mL of a phosphate buffer (37° C., pH 7.8). The result is shown in Table 1.

TABLE 1

| | Dissolution rate of glimepiride (%) | | |
|---|---|---|---|
| | Time | | |
| | 10 minutes | 20 minutes | 30 minutes |
| Example 3 | 91.4 | 96.2 | 98.1 |
| Comparative Example | 54.1 | 71.1 | 78.1 |

As shown in Table 1, the solid preparation of the invention has the improved dissolution property of glimepiride.

EXPERIMENTAL EXAMPLE 2

Dissolution of pioglitazone hydrochloride from the tablet of Example 3 was tested by a paddle method (50 rpm) using 900 mL of a 0.3 M hydrochloric acid-potassium chloride buffer (37° C., pH 2.0). The result is shown in Table 2.

TABLE 2

| | Dissolution rate of pioglitazone hydrochloride (%) | | |
|---|---|---|---|
| | Time | | |
| | 10 minutes | 20 minutes | 30 minutes |
| Example 3 | 66.7 | 93.4 | 101.3 |

As shown in Table 2, the solid preparation of the invention is excellent in the dissolution property of pioglitazone hydrochloride.

INDUSTRIAL APPLICABILITY

The solid preparation of the present invention is useful as a diabetes-treating agent or the like and excellent in the dissolution properties of an insulin sensitizer and an insulin secretagogue.

The invention claimed is:

1. A solid preparation comprising a layer containing pioglitazone or a salt thereof; and a layer containing glimepiride and a Polysorbate 80, wherein the content of Polysorbate 80 is 0.01 to 30 parts by weight based on 100 parts by weight of the solid preparation.

2. The solid preparation according to claim 1, wherein the pioglitazone or salt thereof is pioglitazone hydrochloride.

3. A solid preparation according to claim 1, which comprises a layer containing pioglitazone hydrochloride, and a layer containing glimepiride and Polysorbate 80.

4. The preparation of claim 1, wherein the content of Polysorbate 80 is 0.05 to 20 parts by weight based on 100 parts by weight of the solid preparation.

5. The preparation of claim 1, wherein the content of Polysorbate 80 is 0.2 to 1 parts by weight based on 100 parts by weight of the solid preparation.

* * * * *

UNITED STATES PATENT AND TRADEMARK OFFICE
CERTIFICATE OF CORRECTION

PATENT NO. : 7,700,128 B2 Page 1 of 1
APPLICATION NO. : 10/544581
DATED : April 20, 2010
INVENTOR(S) : Doken et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (711) days Delete the phrase "by 711 days" and insert -- by 831 days --

Signed and Sealed this

Tenth Day of August, 2010

David J. Kappos
*Director of the United States Patent and Trademark Office*